(12) United States Patent
Sullivan et al.

(10) Patent No.: US 9,864,173 B2
(45) Date of Patent: Jan. 9, 2018

(54) SYSTEMS AND METHODS FOR RUN-TIME ALIGNMENT OF A SPOT SCANNING WAFER INSPECTION SYSTEM

(71) Applicant: KLA-Tencor Corporation, Milpitas, CA (US)

(72) Inventors: Jamie M. Sullivan, Eugene, OR (US); Wenjian Cai, Sunnyvale, CA (US); Kai Cao, Fremont, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/004,331

(22) Filed: Jan. 22, 2016

(65) Prior Publication Data

US 2016/0313256 A1 Oct. 27, 2016

Related U.S. Application Data

(60) Provisional application No. 62/150,295, filed on Apr. 21, 2015.

(51) Int. Cl.

| | |
|---|---|
| *G01B 11/00* | (2006.01) |
| *G02B 13/00* | (2006.01) |
| *G01N 21/95* | (2006.01) |
| *G01N 21/956* | (2006.01) |

(52) U.S. Cl.
CPC ..... *G02B 13/0095* (2013.01); *G01N 21/9501* (2013.01); *G01N 21/95607* (2013.01); *G01N 2201/106* (2013.01); *G01N 2201/12* (2013.01)

(58) Field of Classification Search
CPC ........... G01N 21/8806; G01N 21/9501; G01N 2201/106; G01N 2201/0668; G01N 2201/0638; G02B 5/32; G02B 26/123; G02B 27/1086; G02B 27/123; G02F 1/33
USPC ............................ 356/399–401, 237.2–237.6
See application file for complete search history.

(56) References Cited

U.S. PATENT DOCUMENTS

| | | | | |
|---|---|---|---|---|
| 5,864,394 A | * | 1/1999 | Jordan, III | ............. G01N 21/94 257/E21.53 |
| 6,141,038 A | | 10/2000 | Young et al. | |
| 6,236,454 B1 | * | 5/2001 | Almogy | ............. G01N 21/8806 356/237.3 |

(Continued)

OTHER PUBLICATIONS

PCT Search Report for PCT/US2016/028400 dated Jun. 30, 2016, 3 pages.

*Primary Examiner* — Tarifur Chowdhury
*Assistant Examiner* — Isiaka Akanbi
(74) *Attorney, Agent, or Firm* — Suiter Swantz pc llo

(57) ABSTRACT

A spot scanning imaging system with run-time alignment includes a beam scanning device configured to linearly scan a focused beam of illumination across a sample, one or more detectors positioned to receive light from the sample, and a controller communicatively coupled to the beam scanning apparatus, the sample stage, and the one or more detectors. The controller is configured to store a first image, transmit a set of drive signals to at least one of the beam scanning device, the sample stage, or the one or more detectors, compare at least a portion of the second sampling grid to at least a portion of the first sampling grid to determine one or more offset errors, and adjust at least one drive signal in the set of drive signals based on the one or more offset errors such that the second sample grid overlaps the first sample grid.

26 Claims, 13 Drawing Sheets

(56) References Cited

U.S. PATENT DOCUMENTS

| | | |
|---|---|---|
| 6,775,051 B2 | 8/2004 | Sullivan et al. |
| 8,995,746 B2 | 3/2015 | Cao et al. |
| 2005/0210423 A1 | 9/2005 | Liao et al. |
| 2008/0304734 A1 | 12/2008 | Young et al. |
| 2009/0058437 A1 | 3/2009 | Honda et al. |
| 2009/0074286 A1 | 3/2009 | Kitazawa et al. |
| 2011/0280469 A1 | 11/2011 | Lee |
| 2014/0260640 A1* | 9/2014 | Sullivan ............. G01N 29/2418 73/655 |
| 2014/0270471 A1* | 9/2014 | Cao ....................... G06T 7/0004 382/145 |

* cited by examiner

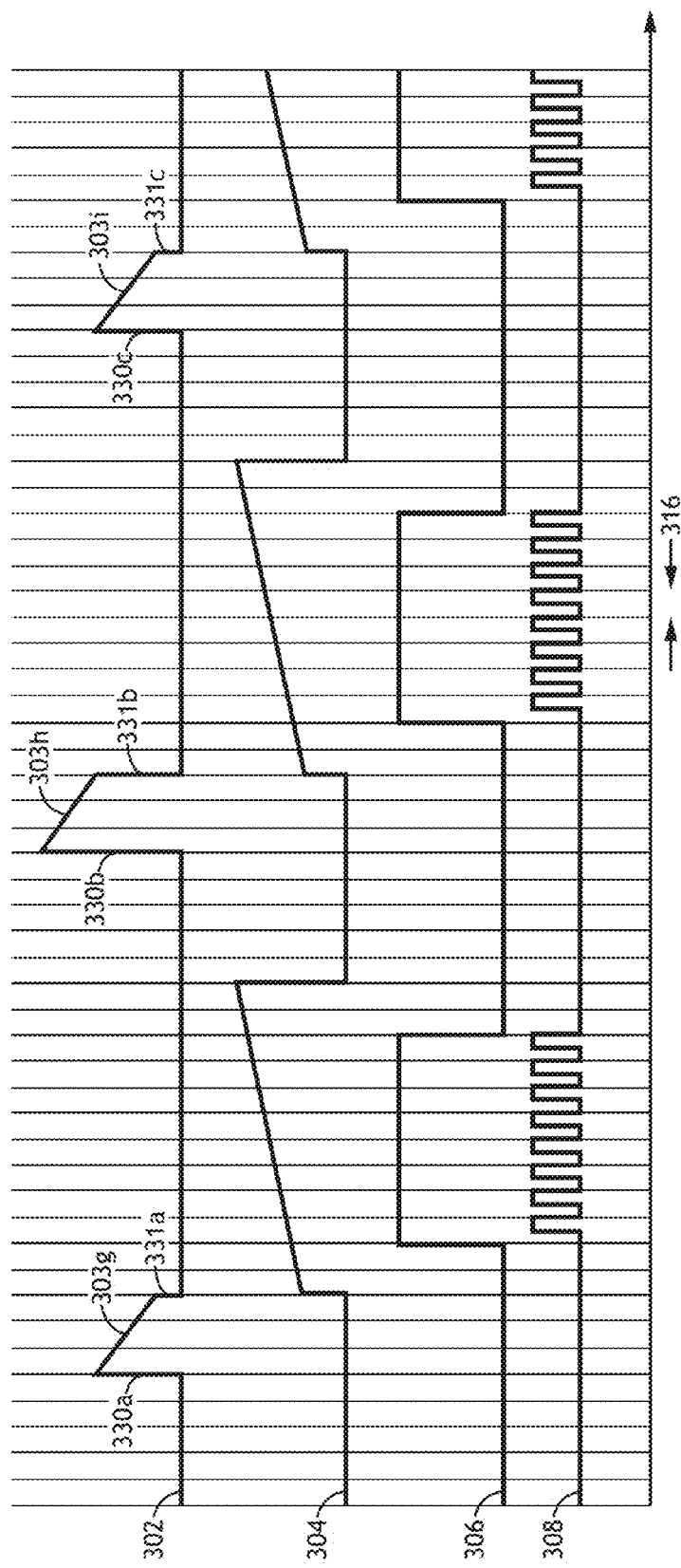

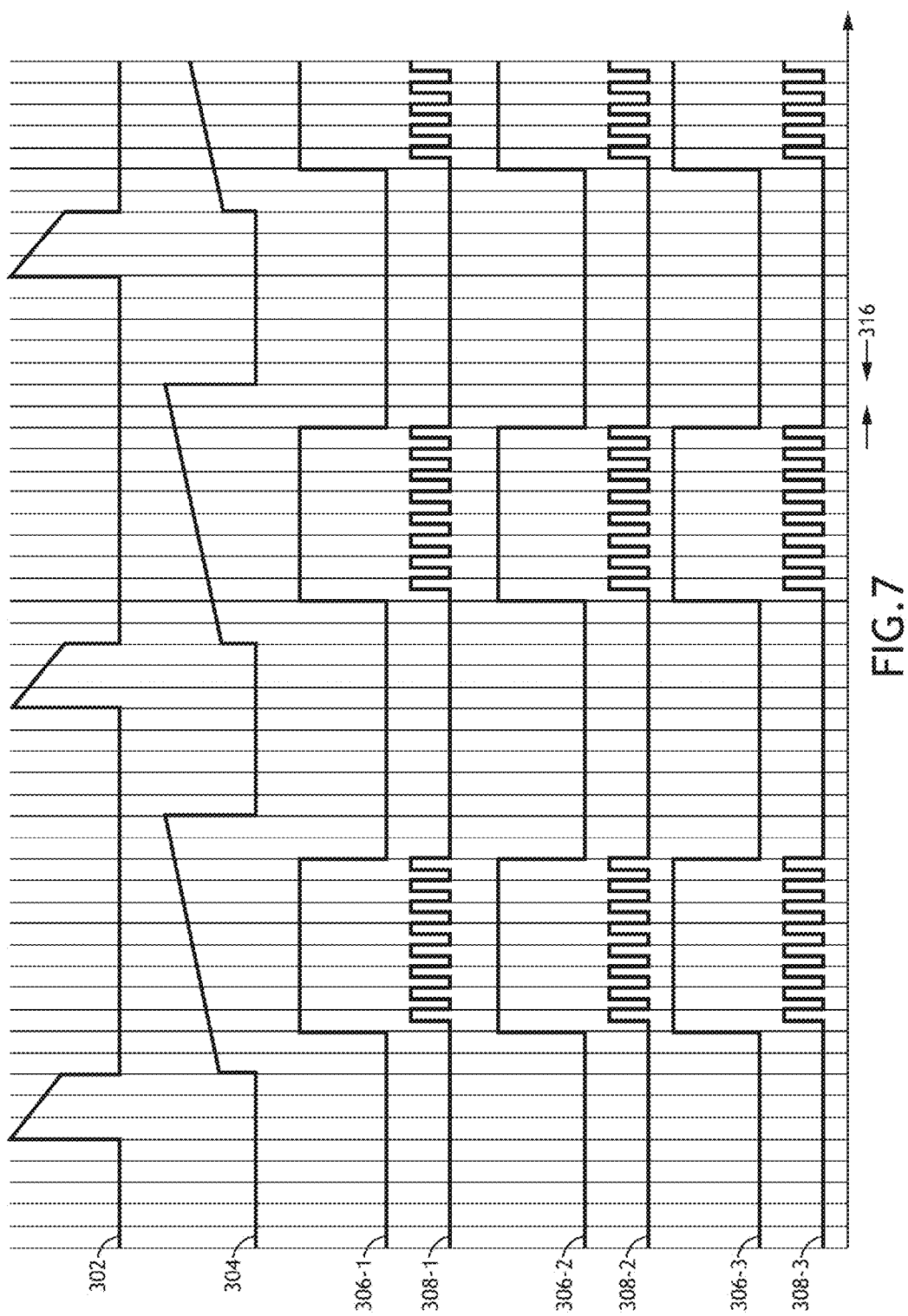

SYSTEMS AND METHODS FOR RUN-TIME ALIGNMENT OF A SPOT SCANNING WAFER INSPECTION SYSTEM

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

Related Applications

For purposes of the USPTO extra-statutory requirements, the present application constitutes a regular (non-provisional) patent application of United States Provisional Patent Application entitled Run Time Alignment For Laser Scanning Imaging, naming Jamie Sullivan, Wenjian Cai, and Kai Cao as inventors, filed Apr. 21, 2015, Application Ser. No. 62/150,295, which is incorporated herein by reference in the entirety.

TECHNICAL FIELD

The present disclosure relates generally to the run-time alignment of an image, and, in particular, to the run-time alignment of an image of a wafer in a spot scanning inspection system.

BACKGROUND

Wafer inspection systems are often used to analyze wafers (or "dies") in order to determine the presence of potential defects. A typical wafer inspection system will generate an image of the die to be analyzed and compare this image to a reference image, which may be taken from a database or the image of another die in the series. The comparison of the two images may be accomplished by several methods, but some form of subtraction is typical. However, the quality of the comparison on the accuracy of the registration of the images, that is to say the ability to sample the two images at nearly identical points. Therefore, it is highly desirable to create systems and methods for the run-time alignment of the sampled locations on a wafer in order to optimize the sensitivity of the wafer inspection system.

The type and geometry of the sensor used to sample a die (i.e. to generate an image of the die) influences the accuracy of the sampling as well as the resistance of the wafer inspection system to errors such as vibration, air currents, and illumination source drift. The noise tolerance is related to the exposure time as well as the time required to capture the data; the higher the bandwidth of a run-time alignment system, the higher the frequency of misalignment errors that can be compensated by the system. For example, the noise tolerance of a two-dimensional sensor (e.g. a CCD camera) is related to the exposure time; the noise tolerance of a 1D sensor is related to the line rate; and the noise tolerance of spot scanning architectures is related to the pixel sampling rate. Spot scanning architectures are therefore capable of producing high quality images with little blur, provided that adequate compensation systems with sufficient bandwidth correction are in place.

SUMMARY

A spot scanning imaging system with run-time alignment is disclosed, in accordance with one or more illustrative embodiments of the present disclosure. In one illustrative embodiment, the system includes a beam scanning device configured to linearly scan a focused beam of illumination across a sample positioned on a sample stage. In another illustrative embodiment, the system includes one or more detectors positioned to receive light from the sample. In another illustrative embodiment, the system includes a controller communicatively coupled to the beam scanning apparatus, the sample stage, and the one or more detectors. In another illustrative embodiment, the controller includes one or more processors configured to execute program instructions to cause the one or more processors to store a first image. In another illustrative embodiment, the center positions of pixels on the first image define a first sampling grid. In another illustrative embodiment, the controller includes one or more processors configured to execute program instructions to cause the one or more processors to transmit a set of drive signals to at least one of the beam scanning device, the sample stage, or the one or more detectors such that the beam is linearly scanned across at least a portion of the sample along one or more linear scan lines. In another illustrative embodiment, the sample is sampled at one or more sampled locations along the one or more linear scan lines based on the set of drive signals to generate a second image. In another illustrative embodiment, the one or more sampled locations define a second sampling grid. In another illustrative embodiment, data associated with the one or more sampled locations corresponds to one or more pixels of the second image. In another illustrative embodiment, the controller includes one or more processors configured to execute program instructions to cause the one or more processors to compare at least a portion of the second sampling grid to at least a portion of the first sampling grid to determine one or more offset errors. In another illustrative embodiment, the controller includes one or more processors configured to execute program instructions to cause the one or more processors to adjust at least one drive signal in the set of drive signals based on the one or more offset errors such that the second sample grid overlaps the first sample grid.

A spot scanning imaging system with run-time alignment is disclosed, in accordance with one or more illustrative embodiments of the present disclosure. In one illustrative embodiment, the system includes an illumination source configured to generate a beam of illumination. In another illustrative embodiment, the system includes an acousto-optic deflector. In another illustrative embodiment, the acousto-optic deflector is configured to generate one or more chirp packets that propagate along a length of the acousto-optic deflector. In another illustrative embodiment, at least a portion of the beam is focused by the one or more chirp packets such that at least a portion of the beam is focused and scanned along a linear path. In another illustrative embodiment, the system includes a relay lens assembly including one or more lenses positioned to relay the focused beam travelling along the linear path to a sample secured on a sample stage. In another illustrative embodiment, the system includes one or more detectors positioned to receive light from the sample. In another illustrative embodiment, the system includes a controller communicatively coupled to the acousto-optic deflector and at least one of the one or more detectors. In another illustrative embodiment, the controller includes one or more processors configured to execute program instructions configured to cause the one or more processors to store a first image. In another illustrative embodiment, the center positions of pixels on the first image define a first sampling grid. In another illustrative embodiment, the controller includes one or more processors configured to execute program instructions configured to cause the one or more processors to transmit a set of drive signals to at least one of the beam scanning device, the sample stage, or the one or more detectors such that the beam is linearly scanned across at least a portion of the sample along one or more linear scan lines. In another illustrative embodiment, the sample is sampled at one or more sampled locations along the one or more linear scan lines based on the set of drive signals to generate a second image. In another illustrative embodiment, the one or more sampled locations define a second sampling grid. In another illustrative embodiment, data associated with the one or more sampled locations corresponds to one or more pixels of the second image. In another illustrative embodiment, the controller includes one or more processors configured to execute program instructions configured to cause the one or more processors to compare at least a portion of the second sampling grid to at least a portion of the first sampling grid to determine one or more offset errors. In another illustrative embodiment, the controller includes one or more processors configured to execute program instructions configured to cause the one or more processors to adjust at least one drive signal in the set of drive signals based on the one or more offset errors such that the second sample grid overlaps the first sample grid.

A method for run-time alignment of a spot scanning sample inspection system is disclosed, in accordance with one or more illustrative embodiments of the present disclosure. In one illustrative embodiment, the method includes generating a beam of illumination. In one illustrative embodiment, the method includes storing a first image. In one illustrative embodiment, the center positions of pixels on the first image define a first sampling grid. In one illustrative embodiment, the method includes transmitting a set of drive signals to at least one of a beam scanning device, a sample stage for securing a sample, or one or more detectors for receiving light from the sample such that the beam is linearly scanned across at least a portion of a sample along one or more linear scan lines. In one illustrative embodiment, the sample is sampled at one or more sampled locations along the one or more linear scan lines based on the set of drive signals to generate a second image. In one illustrative embodiment, the one or more sampled locations define a second sampling grid. In one illustrative embodiment, data associated with the one or more sampled locations corresponds to one or more pixels of the second image. In one illustrative embodiment, the method includes comparing at least a portion of the second sampling grid to at least a portion of the first sampling grid to determine one or more offset errors. In one illustrative embodiment, the method includes adjusting at least one drive signal in the set of drive signals based on the one or more offset errors such that the second sample grid overlaps the first sample grid.

BRIEF DESCRIPTION OF DRAWINGS

The numerous advantages of the disclosure may be better understood by those skilled in the art by reference to the accompanying figures in which:

FIG. 5C is a timing diagram illustrating the adjustment of a chirp-packet drive signal for run-time alignment of a spot scanning wafer inspection system, in accordance with one embodiment of the present disclosure.

FIG. 7 is a timing diagram illustrating drive signals for a multi-spot run-time alignment system, in accordance with one embodiment of the present disclosure.

DETAILED DESCRIPTION

Figure 1:
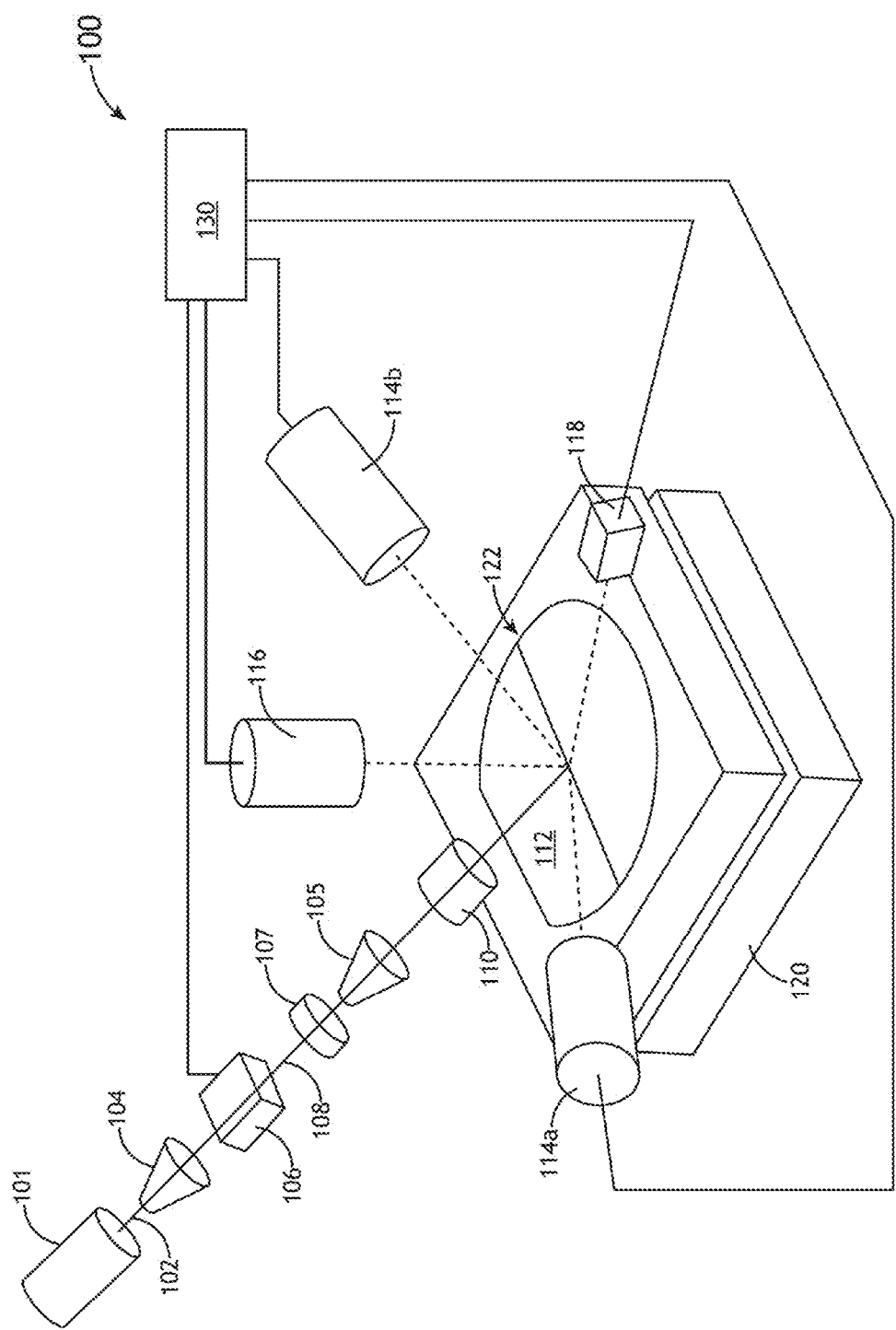
FIG. 1 is a schematic view of a spot scanning wafer inspection system, in accordance with one embodiment of the present disclosure.

Reference will now be made in detail to the subject matter disclosed, which is illustrated in the accompanying drawings. The present disclosure has been particularly shown and described with respect to certain embodiments and specific features thereof. The embodiments set forth herein are taken to be illustrative rather than limiting. It should be readily apparent to those of ordinary skill in the art that various changes and modifications in form and detail may be made without departing from the spirit and scope of the disclosure.

Referring generally to FIGS. 1 through 9, systems and methods for electronic run-time alignment for spot scanning imaging are described, in accordance with one or more embodiments of the disclosure. Embodiments of the present disclosure are directed to modifying the locations of sampled points (i.e. the sampling grid) in a spot scanning system. In some embodiments, the locations of sampled points are modified by controlling the timing of the data acquisition with respect to the timing of the sweep of the illumination beam. In other embodiments, the location of a sampled line is modified by deflecting an illumination beam to independently control the starting location of each line. A spot scanning wafer inspection system is generally described in U.S. Pat. No. 6,775,051 issued on Aug. 8, 2004 and U.S. Pat. No. 8,995,746 issued on Mar. 31, 2015, which are incorporated herein by reference in their entirety. The alignment correction of an image sampling inspection system via mechanical means is generally described in U.S. Pat. No. 6,141,038 issued on Oct. 31, 2000, which is incorporated herein by reference in its entirety.

A spot scanning imaging system may generate an image of a die point by point by scanning illumination from an illumination source (e.g. a laser) across the die and collecting illumination from the die from discrete locations on the die. It is noted herein that illumination may be collected from the die using one or more detectors. It is further noted herein that the physical location of the sampled points defines the sampling grid and further defines the pixels of the image. The combination of point-by-point detection and the use of one or more detectors to gather information from each sampled point enables the generation of highly resolved and highly sensitive images.

A wafer inspection system may detect defects in a die through the generation of a measured image of the die of interest and the comparison of this measured image to a reference image. In some embodiments, the reference image may include an image retrieved from a database. In other embodiments, the reference image may include an image of one or more other dies. In additional embodiments, the reference image may be a computer generated image. The comparison of the two images may be accomplished by any method, such as, but not limited to, image-based subtraction.

One purpose of electronic run-time alignment is to align the sampling grid of the measured image with the reference image such that the sampled locations on a measured object align with corresponding locations on the reference image. In one embodiment, the reference image and the sample image may be further aligned by a subsequent image registration procedure in which features of the sample image are aligned to features on the reference image. Both the reference image and the measured image are digitized such that the images are formed from an array of discrete pixels in which a given pixel represents information associated with an area of the image. In this regard, an image of a physical object (e.g. a wafer) is an approximate representation of the object in which each pixel represents aggregated information associated with a sampled area of the object. For example, a repeating arrangement of sampled locations on a measured object may be represented as an image in which the sampled locations represent the center locations of pixels in a measured image. Each pixel of a measured image may then be directly compared to corresponding pixels of a reference image. The accuracy of a wafer inspection system depends at least in part on the accuracy at which the sample grid of a measured image is aligned to the sample grid of a reference image.

It is recognized herein that the performance of a run-time alignment system may be characterized at least in part by the system bandwidth, which may describe multiple factors including, but not limited to, the speed at which a correction may be applied or the spatial resolution at which a correction may be applied. It is further noted that the bandwidth of systems including mechanical motion may be limited by physical constraints. A second purpose of electronic run-time alignment is to utilize electronic drive signals to enable high-bandwidth alignment with high-speed corrections and high spatial resolution.

FIG. 1 illustrates a spot-scanning imaging system 100 with electronic run-time alignment, in accordance with one or more embodiments of the present disclosure. In one embodiment, an illumination source 101 generates a beam of illumination 102. In another embodiment, a beam deflector 106 transforms the beam 102 into a scanning beam 108. In another embodiment, an objective lens 110 focuses the scanning beam 108 onto the surface of a wafer 112 to generate a scan line 122. It is noted herein that the one or more beam deflectors 106 can include any type of beam deflectors known in the art including, but not limited to, acousto-optic beam deflectors, electro-optic beam deflectors, a polygonal scanner, a resonant scanner, or a galvanometer scanner. A two-dimensional image of a wafer 112 is then generated by moving the sample stage in a direction orthogonal to the direction of the scan line 122 between successive scans.

In one embodiment, one or more beam conditioning elements 104 are positioned prior to the beam deflector 106. The one or more beam conditioning elements 104 may include any optical element known in the art suitable for conditioning the beam 102. For example, the one or more beam conditioning elements 104 may include, but are not limited to, one or more lenses, one or more polarizers, one or more filters, one or more waveplates, or one or more beam shapers. In one embodiment, the one or more beam conditioning elements 104 expand the beam 102 to fill an input aperture of a beam scanner 106. In another embodiment, the one or more beam conditioning elements 104 adjust the polarization of the beam 102. In another embodiment, the one or more beam conditioning elements 104 modify the spatial profile of the beam 102.

In another embodiment, the system 100 includes a relay lens 107 positioned after the beam deflector 106 to collect the scanning beam 108. In one embodiment, a relay lens 107 collimates a focused scanning beam 108 directed from a beam scanner 106 and directs the collimated scanning beam 108 to the one or more optical elements 109. In another embodiment, one or more beam conditioning elements 105 are positioned prior to the objective lens 110. The one or more beam conditioning elements 105 may include any optical element known in the art suitable for conditioning the scanning beam 108. For example, the one or more beam conditioning elements 105 may include, but are not limited to, one or more lenses, one or more magnification controllers, one or more polarizers, one or more filters, one or more waveplates, or one or more beam shapers. In one embodiment, the one or more beam conditioning elements 105 includes a magnification controller suitable for adjusting the focused size of the scanning beam 108 on the wafer 112.

It is noted herein that the system 100 may simultaneously scan multiple scanning beams 108 across a wafer 112. It is further noted that multiple scanning beams 108 may be generated using any method known in the art. For example, multiple scanning beams 108 may be generated using one or more diffractive optical elements. In one embodiment, one or more diffractive optical elements positioned prior to the objective lens 110 split a scanning beam 108 into one or more scanning beams 108. In another embodiment, one or more optical elements (e.g. one or more diffractive optical elements) rotate the focal plane of the objective lens 110 such that a 2-D array of scanning beams 108 is simultaneously in focus on the wafer 112.

In another embodiment, the system 100 includes a stage assembly 120 suitable for securing and positioning a wafer 112. The stage assembly 120 may include any sample stage architecture known in the art. In one embodiment, the stage assembly 120 includes a linear stage. In another embodiment, the stage assembly 120 includes a rotational stage. The wafer 112 may include but is not limited to, an unpatterned semiconductor wafer. It is noted herein that a two-dimensional image of a wafer 112 may be generated by translating the wafer 112 between successive scans along the two or more scan lines 122. It is further noted that the one or more beam deflectors 106 can include any type of beam deflectors known in the art including, but not limited to, one or more acousto-optic beam deflectors, one or more electro-optic beam deflectors, one or more polygonal scanners, one or more resonant scanners, or one or more galvanometer scanners.

It is noted herein that the illumination source 101 may include any illumination source known in the art. By way of non-limiting example, the illumination source 101 may include, but is not limited to, any laser system, including one or more laser sources, configured to generate a set of wavelengths or a wavelength range. The laser system may be configured to produce any type of laser radiation such as, but not limited to infrared radiation, visible radiation and/or ultraviolet (UV) radiation. In one embodiment, the illumination source 101 is a laser system configured to emit continuous wave (CW) laser radiation. In another embodiment, the illumination source 101 is a pulsed laser source. In another embodiment, the illumination source 101 is configured to produce a modulated output. For example, the illumination source 101 may be modulated with an acousto-optic or an electro-optic modulator to produce temporally shaped illumination.

In another embodiment, the illumination source 101 includes one or more excimer laser systems. By way of non-limiting example, the illumination source 101 may include, but is not limited to, an excimer laser with molecular fluorine as an active gas, which provides emission of 157 nm laser light. In another embodiment, the illumination source 101 includes one or more diode laser systems (e.g., one or more diode for emitting light at 445 nm).

In one embodiment, the illumination source 101 includes one or more diode lasers. In another embodiment, the illumination source 101 includes one or more diode-pumped solid state lasers. For example, the illumination source 101 may include a diode-pumped solid state laser with a wavelength including, but not limited to, 266 nm. In another embodiment, the illumination source 101 includes one or more frequency converted laser systems. For instance, the illumination source 101 may include, but is not limited to, a frequency converted laser suitable for emitting light having a nominal central illumination wavelength of 532 nm coupled with a frequency-doubling system that produces illumination with a 266 nm central wavelength.

In one embodiment, one or more detectors are positioned to simultaneously collect reflected and/or scattered light from two or more scan lines 122 on the wafer 112. In one embodiment, a detector 118 is positioned to receive illumination reflected from the wafer 112. The detector 118 may operate as a "reflectivity sensor" or a "brightfield sensor". For example, the detector 118 may be used to generate a reflectivity map of the sample. As another example, the detector 118 may be used to monitor wafer 112 characteristics including, but not limited to, structure height, film thickness, or dielectric constant. In another embodiment, a detector 116 positioned normal to the surface of the wafer 112 detects light scattered in a direction normal to the wafer surface. Additionally, a detector 116 may detect light directly reflected from structures on the wafer surface. In one embodiment, detectors 114a and 114b detect light scattered from the wafer 112. In this regard, one or more detectors 114a, 114b may collect forward scattered light, laterally scattered light, or backward scattered light according the detector position relative to the sampled point. It is noted herein that the one or more detectors 114a, 114b, 116, or 118 may include any detector known in the art. For example, detectors 114a, 114b, 116 or 118 may include, but are not limited to, CCD detectors, photodiodes, avalanche photodiodes (APDs) and/or or photomultiplier tubes (PMTs). It is further noted that the one or more detectors 114a, 114b, 116, or 118 may be multi-channel detectors configured to simultaneously detect signals from multiple detection regions on the wafer 112 (e.g., one or more regions of one or more scan lines 122). It is contemplated herein that cross-talk between channels of a detector (e.g., 114a, 114b, 116, or 118) may be minimized by separating the detection regions on a wafer 112 such that illumination (e.g., scattered light) from a given detection region is only detected by a single channel.

Figure 2:
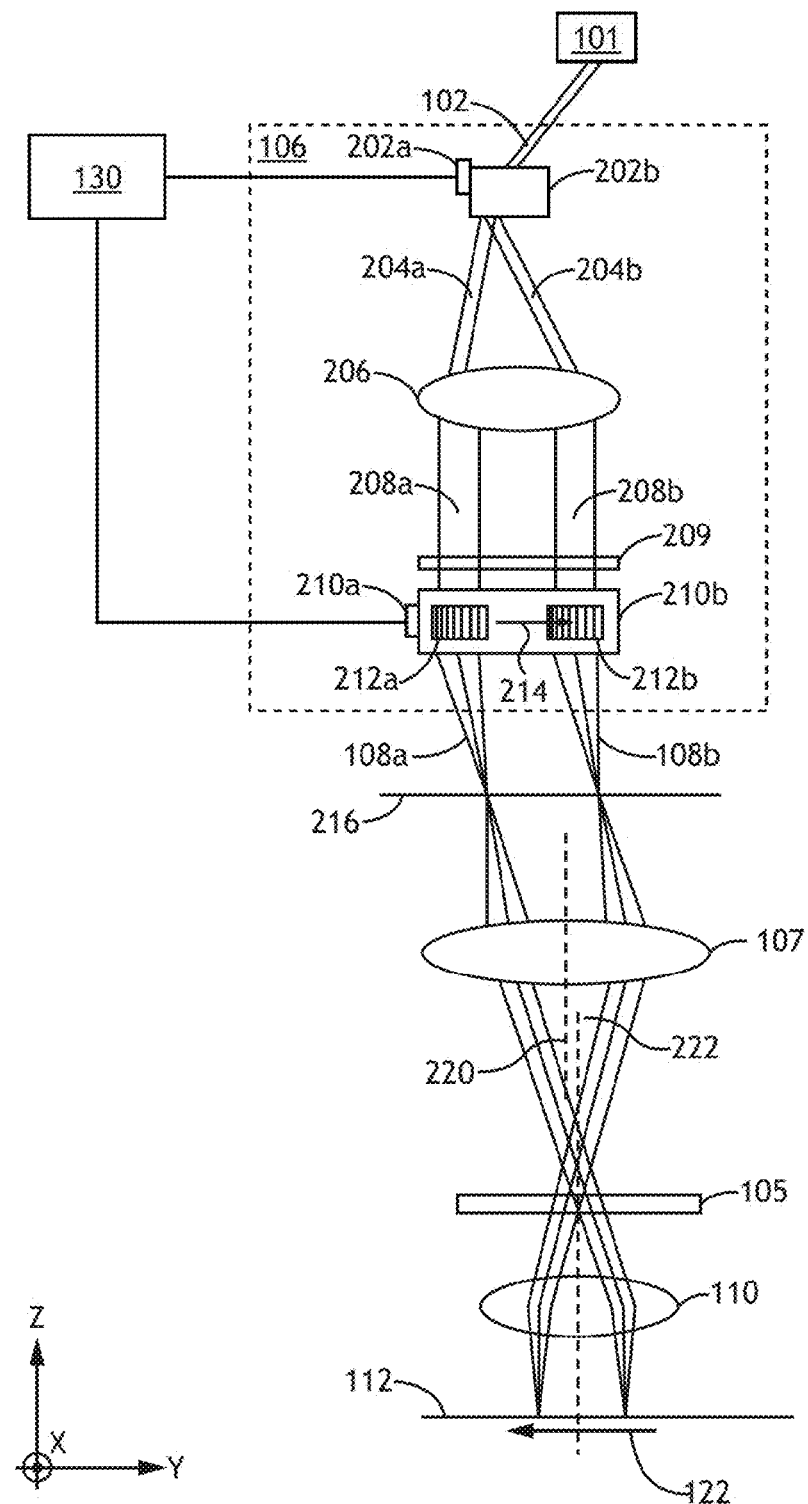
FIG. 2 is a schematic view of a portion of a spot scanning wafer inspection system illustrating the use of acousto-optic deflectors to linearly scan a beam, in accordance with one embodiment of the present disclosure.

FIG. 2 illustrates beam paths associated with a spot scanning system, in accordance with one or more embodiments of the present disclosure. In one embodiment, a beam 102 generated by the illumination source 101 is incident on a beam deflector. The beam deflector sweeps the beam 102 across a range of angles that define an angular spread. For example, the beam deflector deflects a beam 102 from a first position 204a to a second position 204b. The beam deflector may include any beam deflector known in the art. For example, the beam deflector may be formed from, but is not limited to, an acousto-optic deflector, an electro-optic deflector, a polygonal deflector, a resonant deflector, or a galvanometer deflector. In one embodiment, the beam deflector is an acousto-optic deflector formed from a solid medium 202b coupled with a transducer 202a configured to generate ultrasonic waves that propagate through the solid medium 202b. Properties of the solid medium 202b such as the refractive index are modified by the propagating wave such that the beam 102 is deflected upon interaction with the solid medium 202b according to the wavelength of the ultrasonic waves. Furthermore, the ultrasonic waves propagate through the solid medium 202b at the velocity of sound in the medium and have a wavelength related to the frequency of the drive signal as well as the velocity of sound in the solid medium 202b. In one embodiment, the transducer 202a generates ultrasonic waves in response to a drive signal generated by a controller 130.

In one embodiment, a lens assembly 206 translates the angular sweep of the beam 102 to a linearly sweeping scanning beam 108 directed from the lens assembly 206. In one embodiment, a lens assembly 206 collimates the scanning beam 108. In another embodiment, the one or more lenses of the lens assembly 206 modify the spatial profile of the scanning beam 108. In another embodiment, the lens assembly 206 expands the diameter of the scanning beam 108.

In one embodiment, the scanning beam 108 is directed to an acousto-optic deflector 210 configured as a traveling lens. A transducer 210a communicatively coupled to the controller 130 generates a chirp packet of ultrasonic waves with linearly varying frequency that propagates through a solid medium 210b along a scan direction 214. The chirp packet operates as a traveling cylindrical lens such that a scanning beam 108 incident on the chirp packet is focused to a position on a line 216; portions of a light beam incident on relatively low frequency portions of the chirp packet are deflected less than portions of a light beam incident on relatively high frequency portions of the chirp packet. In one embodiment, a cylindrical lens 209 focuses the scanning beam 108 in a plane orthogonal to the direction of focus induced by the chirp packet. In this regard, the axis of the cylindrical lens 209 is oriented parallel to the scan direction 214. A cylindrical lens 209 may be placed either before the acousto-optic deflector (e.g. as shown in FIG. 2) or directly after the acousto-optic deflector. In one embodiment, the position and rate of the linear sweep of scanning beam 108 are synchronized with the propagation of a chirp packet. In this regard, a beam at position 208a may be incident on a travelling chirp packet at position 212a; as the chirp packet propagates from position 212a to 212b, the beam at position 208a correspondingly propagates from position 208a to position 208b. As a result, a scanning beam 108 directed from a chirp packet is focused on and linearly scanned along a line 216. It is noted herein that the width of a chirp packet may be less than the length of the solid medium 210b. It is further noted that multiple chirp packets may propagate through the solid medium 210b at the same time in sequence.

In another embodiment, the beam scanner 106 is formed from a lens and a single acousto-optical deflector operating in "flood mode". In this regard, the lens assembly 206 expands the beam 102 and illuminates the full length of the acousto-optical deflector with a stationary beam 102. One or more propagating chirp packets may then be continually illuminated by a portion of the stationary beam 102; portions of the beam 102 not incident on the one or more propagating chirp packets remain unfocused by the acousto-optical deflector.

In one embodiment, a relay lens 107 collimates the scanning beam 108 and an objective lens 110 focuses the scanning beam 108 onto the wafer 112. In one embodiment, the relay lens 107 and the objective lens 110 are positioned in a telecentric configuration. In another embodiment, the relay lens 107 and the objective lens 110 share a common optical axis. In another embodiment, the optical axis 222 of the objective lens 110 is shifted from, but parallel to, the optical axis 220 of the relay lens 107. In this way, the optical axis 222 of the objective lens 110 may be centered on the scan line 122 of the focused scanning beam 108 on the wafer 112. In some embodiments, the system 100 may further include additional optical elements including, but not limited to, prisms and/or mirrors, positioned between the relay lens 107 and the objective lens 110 . By way of non-limiting example, the system 100 may include one or more mirrors configured to center the pupil of the relay lens 107 on the objective lens 110.

Figure 3:
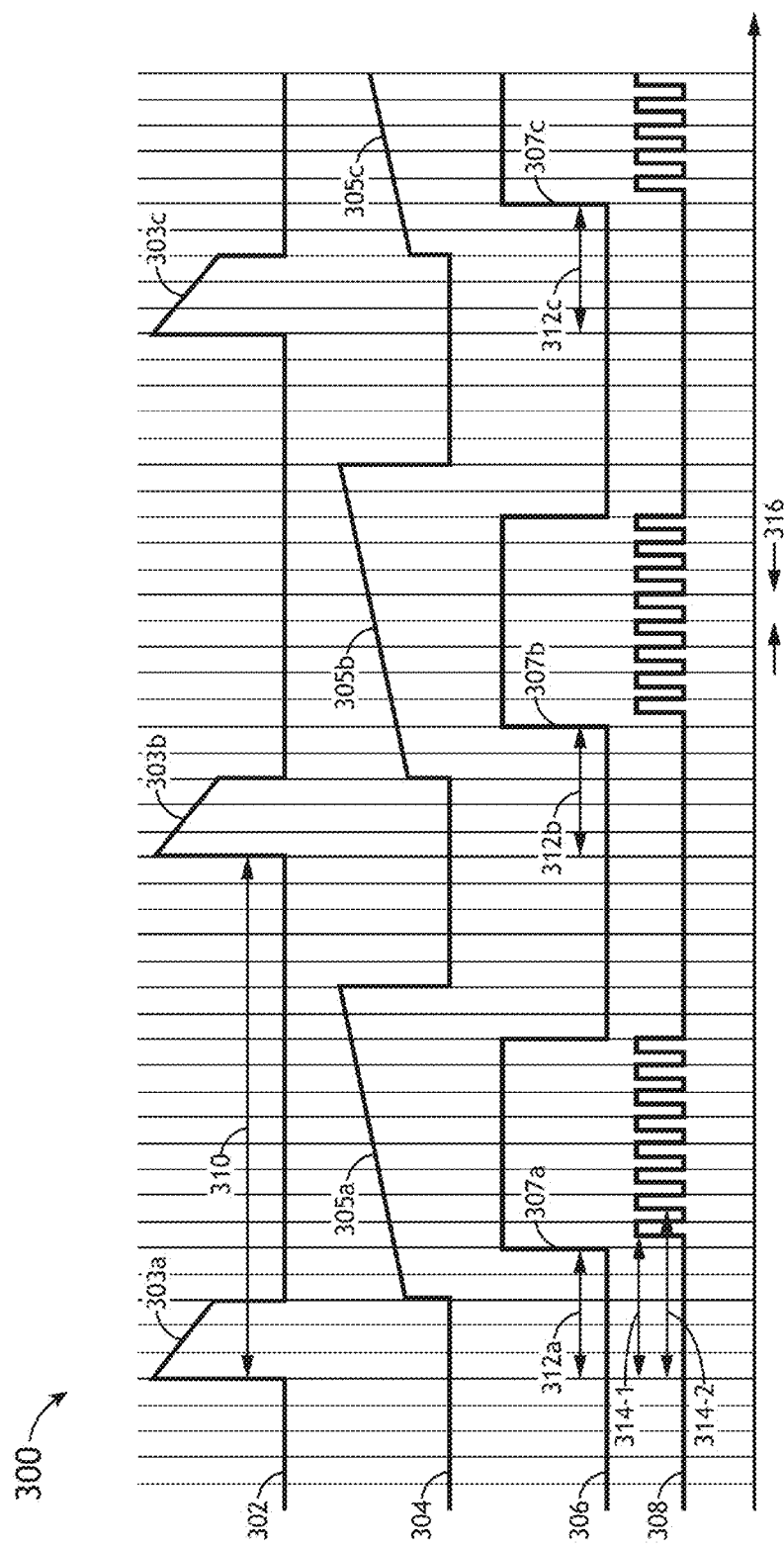
FIG. 3 is a timing diagram illustrating drive signals for components included in a spot scanning wafer inspection system, in accordance with one embodiment of the present disclosure.

FIG. 3 is a timing diagram 300 illustrating drive signals for scanning and image acquisition associated with three linear scans to generate three columns of pixels of a measured image, in accordance with one or more embodiments of the present disclosure. In one embodiment, a chirp-packet drive signal 302 transmitted to the transducer 210a of the acousto-optical deflector defines the linearly varying frequencies of ultrasonic waves associated with chirp packets. The chirp-packet drive signal 302 includes a series of chirp-packet frequency ramps 303 such that each chirp-packet frequency ramp 303a, 303b, 303c corresponds to a chirp packet. Accordingly, each chirp-packet frequency ramp 303a, 303b, 303c corresponds to a linear scan of the scanning beam 108 to generate a column of pixels in a measured image. In one embodiment, a chirp-packet frequency ramp associated with a chirp-packet drive signal 302 defines a start frequency, an end frequency, and a bandwidth associated with a chirp packet. In another embodiment, a width of the chirp-packet frequency ramp corresponds to a width of the chirp packet. In another embodiment, chirp-packet frequency ramps 303a, 303b, 303c are separated by a delay 310 such that delay 310 describes a delay between successive scans of scanning beam 108.

In another embodiment, a beam-scanning drive signal 304 transmitted to the transducer 202a of the beam deflector controls the deflection of the scanning beam 108 onto the chirp packet. The beam-scanning drive signal 304 includes a series of beam-scanning frequency ramps to control the frequency of ultrasound waves in the solid medium 202b and thus the deflection angle of the beam 102. In this regard, beam-scanning frequency ramp 305a controls the position of scanning beam 108 with respect to a chirp packet associated with chirp-packet frequency ramp 303a, beam-scanning frequency ramp 305b controls the deflection of scanning beam 108 onto a chirp packet associated with chirp-packet frequency ramp 303b, and beam-scanning frequency ramp 305c controls the deflection of scanning beam 108 onto a chirp packet associated with chirp-packet frequency ramp 303c.

It is noted herein that a beam-scanning drive signal 304 is not necessary for all embodiments of the present disclosure. As one example, a system 100 includes a single acousto-optic deflector operating in "flood mode" such that a stationary beam 102 illuminates the full length of the acousto-optical deflector and one or more propagating chirp packets are continually illuminated.

In another embodiment, an image acquisition drive signal 306 transmitted to one or more detectors (e.g. 114a, 114b, 116 or 118) defines a data acquisition window associated with linear scans of the scanning beam 108 across a wafer 112. In one embodiment, the image acquisition drive signal 306 includes a series of image acquisition pulses such that one or more detectors (e.g. 114a, 114b, 116, or 118) acquire data during an image acquisition pulse. In this regard, image acquisition pulse 307a defines an image acquisition window for chirp pulse associated with chirp-pulse frequency ramp 303a, image acquisition pulse 307b defines an image acquisition window for chirp pulse associated with chirp-pulse frequency ramp 303b, and image acquisition pulse 307c defines an image acquisition window for chirp pulse associated with chirp-pulse frequency ramp 303c. In another embodiment, image acquisition pulses occur at a delay (e.g. 312a, 312b, and 312c) from the start of a chirp-packet frequency ramp.

In another embodiment, a sampling drive signal 308 transmitted to one or more detectors (e.g. 114a, 114b, 116 or 118) controls sampling times within the image acquisition windows. The location of a given sampled position on the wafer 112 may be determined by a sample spot delay from the start of the image acquisition drive signal 306 and a pulse within the sampling drive signal 308. In one embodiment, a sample spot delay 314-1 determines a first sampled location and a sample spot delay 314-2 determines a second sampled location. It is noted herein that the collection of data from any detectors (e.g. 114a, 114b, 116 or 118) may be performed using any method known in the art. For example, the sampling drive signal may trigger an analog to digital converter configured to digitize the output of a detector (e.g. 114a, 114b, 116 or 118). In another embodiment, the sampling drive signal 308 includes pulses at a fixed repetition rate corresponding to a sampling clock of an analog to digital converter. In another embodiment, sample spot delays may be individually controlled to provide spot-by-spot control of the sampling position.

In one embodiment, the wafer 112 is translated by the sample stage 120 in a direction orthogonal to the beam scan direction such that each linear scan may be performed on a new location of the wafer 112. In general, the sampling grid of the wafer 112 is defined by both the sampling rate of the sampling drive signal 308 as well as the translation of the sample stage 120. In another embodiment, one or more linear scans are performed prior to translation of the wafer 112. Multiple scans of scanning beam 108 may be desirable, for example, to reduce system noise.

The sampling grid defining the locations of sampled points on a wafer 112 may become misaligned relative to the sampling grid of a reference image as a result of multiple factors including, but not limited to, original alignment errors when positioning a wafer 112, mechanical vibrations, air wiggle, air currents, and/or drift of the scanning beam 108. In general, the bandwidth of a run-time alignment system characterizes the speed and sensitivity at which a run-time alignment system can correct alignment errors. In one embodiment, alignment errors are mitigated on a line-by-line basis. In this regard, alignment correction may be individually performed for every linear scan of the scanning beam 108. In one embodiment, a first linear scan is performed to determine a course alignment of the sample grid of the wafer 112. Adjustments to the wafer 112 position may then be initiated by the image acquisition drive signal 306, and/or the sampling drive signal 308. A second linear scan is then performed to generate a final image such that the sample grid of the wafer 112 is optimally aligned with the sample grid of a reference image. In another embodiment, alignment errors are continually mitigated on a point-by-point basis. In this regard, feedback from sampled locations is continually utilized to adjust the sampling locations at subsequent scan locations.

FIGS. 4 through 8 describe run-time alignment correction, in accordance with one or more embodiments of the present disclosure. It is noted herein that the system 100 may apply high-bandwidth electronic run-time alignment by directly modifying the deflection angle of a scanning beam 108 or the timing at which reflected and/or scattered light collected from the wafer 112 is sampled. In this regard, the speed of corrections applied by the system 100 is primarily dependent on the clock-speed of the controller 130. In one embodiment, the start and end positions of a scan line 216 are modified through adjustments of the delay between the chirp-packet drive signal 302 and the image acquisition drive signal 306. In one embodiment, the minimum adjustment of the delay is the period of the time cycle 316 associated with the drive signals. An adjustment of the delay by one time cycle 316 may correspond to a fraction of the period between sampling pulses associated with drive signal 308 and may further correspond to a modification of the location of a sampled point on a measured image of a fraction of a pixel. In this regard, sub-pixel real-time alignment may be performed. The corresponding adjustment of the position of sampled locations on a wafer 112 is related to the speed at which beam 108 is scanned across the wafer 112, which is in turn related to the propagation speed of a chirp packet through the solid medium 210b. A negative shift of the image acquisition drive signal 306 with respect to the chirp-packet drive signal 302 shifts the locations of sampled positions on the wafer 112 towards the start of the scan line 122. Similarly, a positive shift of the image acquisition drive signal 306 with respect to the chirp-packet drive signal 302 shifts the locations of sampled positions on the wafer 112 towards the end of the scan line 122. It is noted herein that the scan direction on the wafer 112 may be opposite to the direction of the intermediate scan line 216 (e.g. as shown in FIG. 2).

In another embodiment, the locations of each sampled point are individually adjusted through modification of the sampling drive signal 308. The sample spot delay for each sampled location on the wafer 112 may be adjusted in order to optimally align the sample grid of the wafer 112 with the sample grid of the reference image. A decrease in sample spot delay shifts the sampled location in the +y direction along the scan line 122 on the wafer 112 and an increase in sample spot delay shifts the sampled location in the −y direction along the scan line 122. In another embodiment, both the image acquisition drive signal delay and the sample spot delay for each sampled location are simultaneously adjusted during electronic run-time alignment. In this regard, the system 100 may perform high-bandwidth pixel-by-pixel alignment corrections.

Figure 4A:
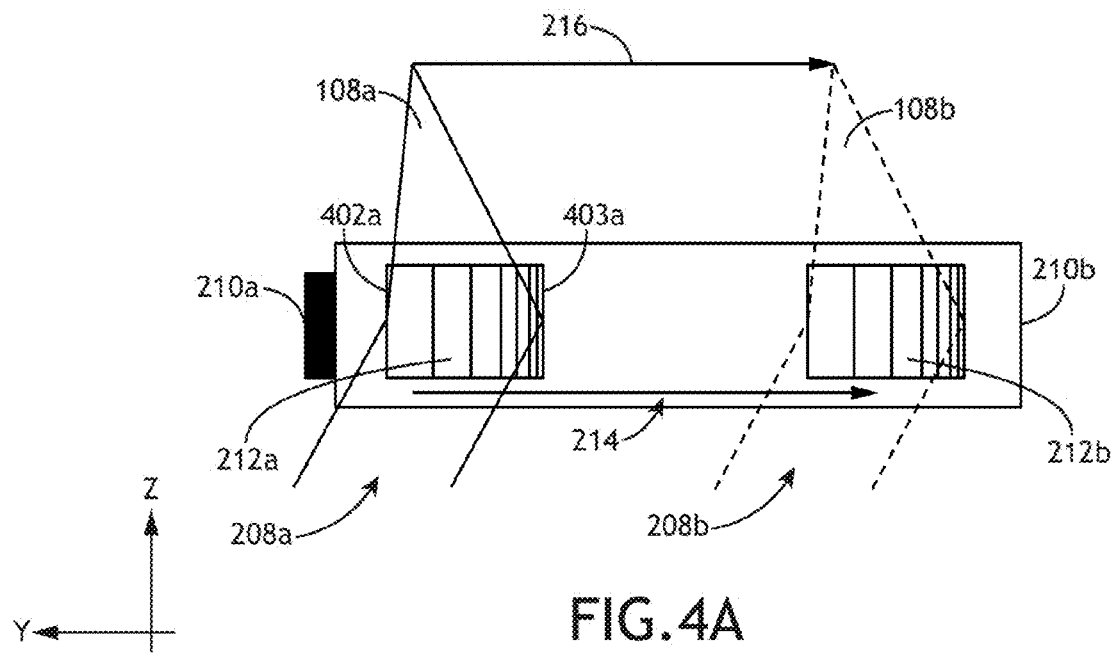
FIG. 4A is a schematic view of an acousto-optic deflector configured to have a propagating chirp packet that acts as a travelling lens, in accordance with one embodiment of the present disclosure.
Figure 4B:
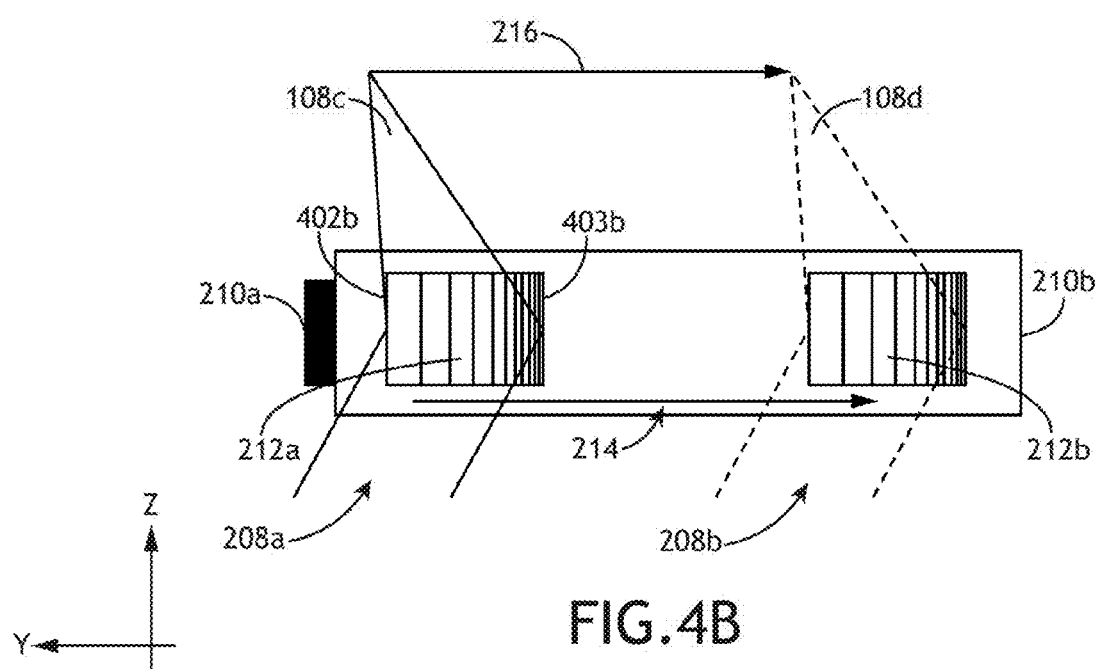
FIG. 4B is a schematic view of an acousto-optic deflector configured to have a propagating chirp packet that acts as a travelling lens, in accordance with one embodiment of the present disclosure. The start and end frequencies of the chirp packet are increased relative to the chirp packet in FIG. 5a in order to shift the start and end locations of a scan line.

Referring to FIGS. 4A and 4B, in one embodiment, the start and end positions of a scanning beam 108 during a linear scan are modified through an adjustment of the start and end frequencies 402 and 403 of a chirp packet. This modification of the start and end frequencies modifies the degree to which chirp packet deflects and focuses the scanning beam 108 from position 108a along an intermediate scan line 216 to position 108b. FIG. 4A illustrates a simplified schematic of an acousto-optic deflector configured with a chirp packet with a first set of start and end frequencies 402a and 403a, in accordance with one or more embodiments of the present disclosure. This chirp packet operates as a travelling lens that propagates along the direction 214 from position 212a to position 212b. FIG. 4B illustrates a simplified schematic of an acousto-optic deflector configured with a chirp packet with a second set of start and end frequencies 402b and 403b that also propagates along the direction 214 from position 212a to position 212b, in accordance with one or more embodiments of the present disclosure. The focused position of the scanning beam 108 is thus shifted in the +y direction in FIG. 4B relative to FIG. 4A based on differences between the start and end frequencies 402 and 403. In this way, the entire scan line 216 is shifted in the +y direction and the locations of the sampled points will be correspondingly shifted. In another embodiment, the start and end frequencies 402 and 403 of a chirp packet may be decreased to shift the start and end locations of a scan line 216 in the −y direction. In one embodiment, the start and end frequencies 402 and 403 for a given chirp packet are transmitted by the controller 130 to the transducer 210a in the drive signal 304. It is noted herein that the scan direction on the wafer 112 may be opposite to the direction of the intermediate scan line 216 (e.g. as shown in FIG. 2). High-bandwidth run-time alignment of a sample grid of a wafer 112 is thus achieved by modifying the start and end positions of each scan line 216. It is further noted that beam deflectors that operate without physical motion of an optical element (e.g. as shown in FIGS. 4A and 4B) may provide higher-bandwidth corrections than beam deflectors that include physical motion of an optical element (e.g. a reflective or a refractive element).

It is noted herein that the focal position of a scanning beam 108 in the y direction is related at least in part to the bandwidth of the chirp packet. A modification of the start and end frequencies 402 and 403 in order to adjust focal position along the scan line 216 in the y direction is thus configured to maintain a constant bandwidth such that focus in the z direction is maintained during the scan.

Figure 5A:
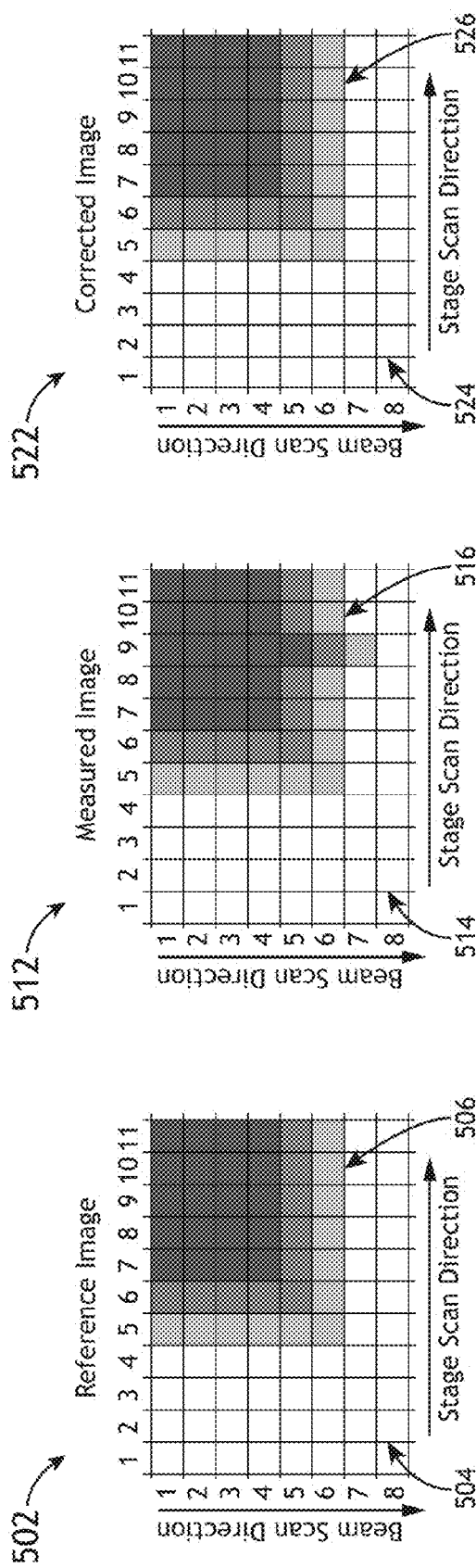
FIG. 5A is a conceptual diagram illustrating run-time alignment of an error along the beam scan direction of a measured image, in accordance with one embodiment of the present disclosure.
Figure 5B:
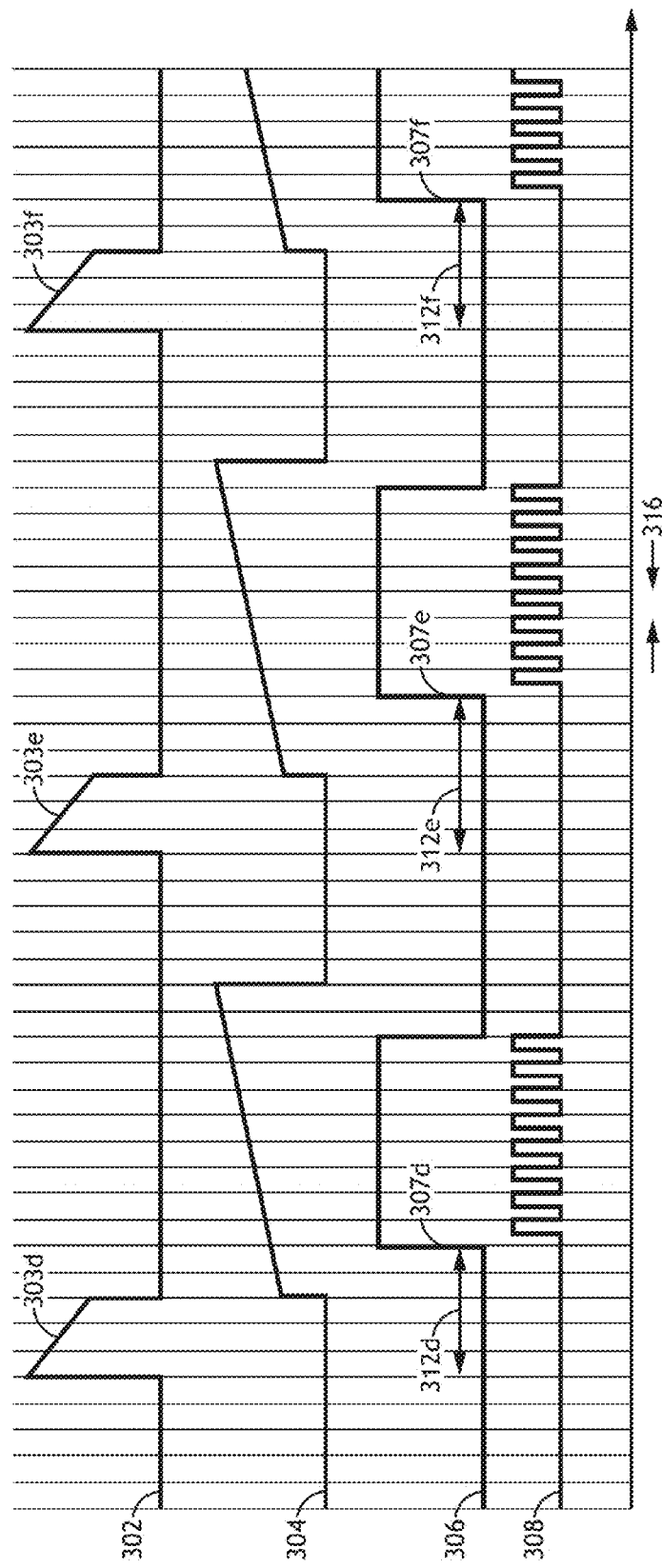
FIG. 5B is a timing diagram illustrating the adjustment of a relative delay between a chirp-packet drive signal and an image acquisition signal for run-time alignment of a spot scanning wafer inspection system, in accordance with one embodiment of the present disclosure.

In one embodiment, each pixel of an image of a wafer 112 is associated with a sample of a single location of the wafer 112. A column of the image is generated by scanning a spot across a wafer 112 in the y-direction and collecting reflected and/or scattered light from the wafer 112 at multiple locations during a scan to generate a column of pixels. Additional columns are generated by translating the sample in the x-direction and performing additional scans. FIGS. 5A through 5C illustrate run-time alignment to correct an error in the y-direction (e.g. the direction along the linear scan) of a sampling grid associated with a measured object, in accordance with one or more embodiments of the present disclosure.

Referring to FIG. 5A, a reference image 502 with a reference sampling grid 504 includes multiple object pixels 506 associated with a reference feature. A measured image 512 without run-time alignment includes multiple object pixels 516 associated with a measured feature. The measured sampling grid 514 without run-time alignment defining locations of sampled points is misaligned with respect to the reference sampling grid 504. Specifically, object pixels 516 associated with a linear scan in column 9 of measured image 512 are shifted by a length approximately equal to the pixel length with respect to reference image 502. Such a misalignment of the measured sampling grid 514 may, by way of non-limiting example, be caused by vibration of the sample stage 120 during the measurement process. Run-time alignment adjusts the positions of sampled locations on the measured object to obtain a corrected image 522 with a corrected sampling grid 524 aligned with the reference sampling grid 504. In the corrected image 522, object pixels 526 associated with the measured object are properly aligned.

FIG. 5B illustrates a timing diagram associated with run-time alignment to produce the corrected image 522, in accordance with one or more embodiments of the present disclosure. According to FIG. 5A, the pixels in column 9 of the measured image 512 are shifted in the −y direction by one pixel. The misalignment of pixels in column 9 of the measured image 512 is corrected by decreasing the delay associated with the image acquisition window for column 9, which initiates sampling earlier in the scan of scanning beam 108 for column 9. Specifically, columns 1-8 of the corrected image 522 are obtained with a nominal delay 312d between a chirp-packet frequency ramp 303d and an image acquisition signal 307d. Column 9 of the corrected image 522 is obtained with a modified delay 312e between chirp-packet frequency ramp 303e and image acquisition signal 307e. Delay 312e is increased relative to delay 312d by one time cycle 316, which corresponds to one pixel on the measured image 512. Columns 10 and 11 of the corrected image 522 are obtained using delay 312f between chirp-packet frequency ramp 303f and image acquisition signal 307f, which is equal to the nominal delay 312d.

FIG. 5C illustrates an alternative timing diagram associated with run-time alignment to produce the corrected image 522, in accordance with one or more embodiments of the present disclosure. The misalignment of pixels in column 9 of measured image 512 is corrected by modifying the start and end positions of the scanning beam 108 during the linear scan. The start and end positions of the scanning beam 108 during the linear scan are controlled by the start and end frequencies 402 and 403 of a chirp packet. Specifically, columns 1-8 of the corrected image 552 are obtained with nominal values of chirp-packet drive signal 302 levels 330a and 330b, corresponding to nominal start and end frequencies (e.g. 402a and 403a). Column 9 of the corrected image is obtained with modified values of chirp packet drive signal 302 levels 330b and 331b, corresponding to modified start and end frequencies (e.g. 402b and 403b). The start and end frequencies (e.g. 402b and 403b) are modified such that the bandwidth of the chirp packet remains constant for all scan lines. In this regard, the deflection angle of the scanning beam 108 for column 9 of the corrected image 522 is adjusted. Columns 10 and 11 of the corrected image 522 are obtained with chirp-packet drive signal 302 levels 330c and 331c, which are equivalent to nominal values 330a and 331a.

Figure 6A:
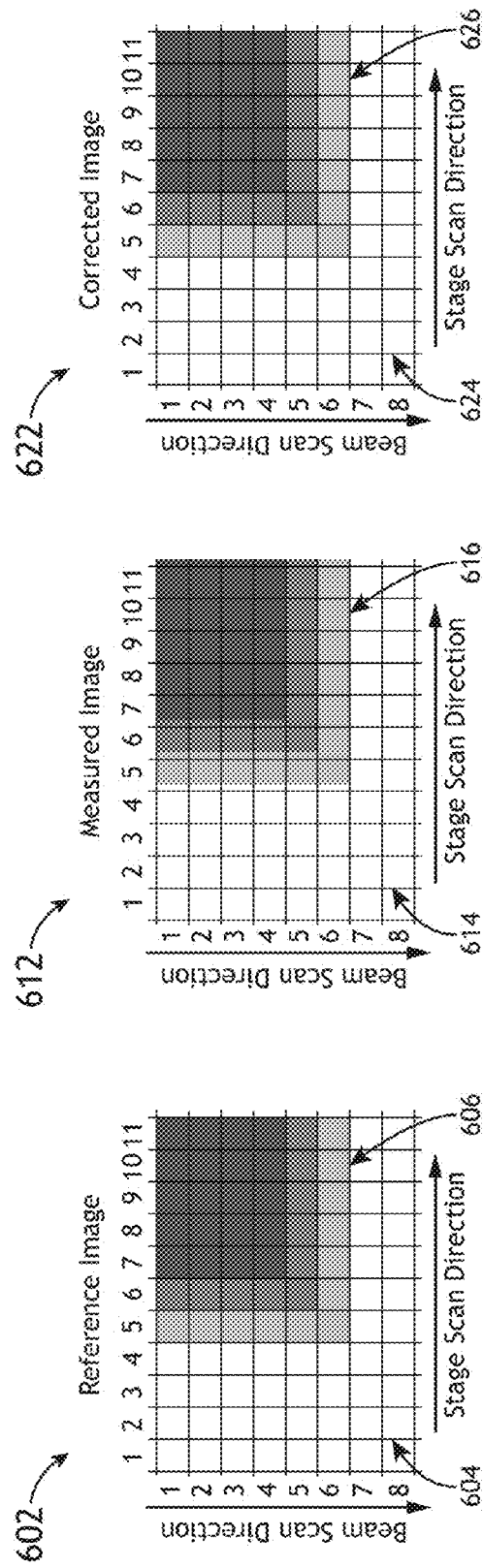
FIG. 6A is a conceptual diagram illustrating run-time alignment of an error along the stage scan direction of a measured image, in accordance with one embodiment of the present disclosure.
Figure 6B:
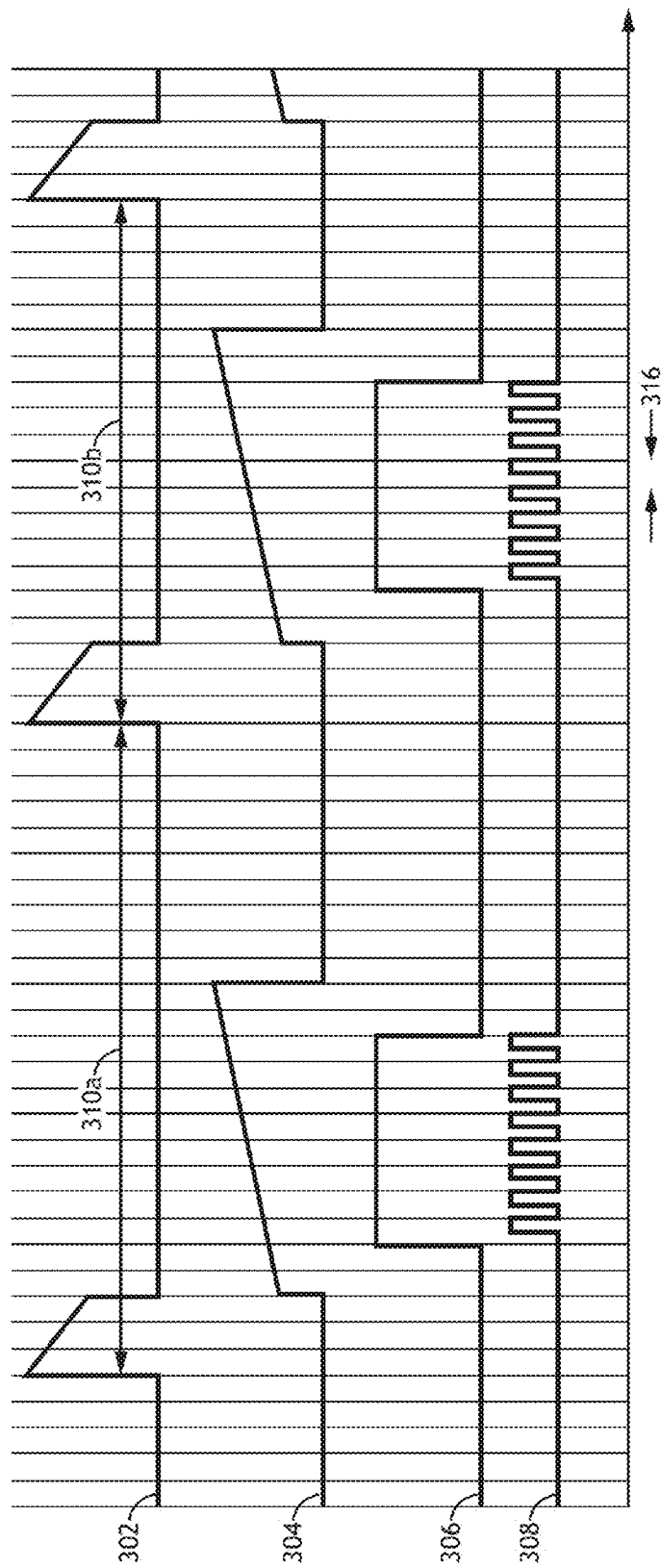
FIG. 6B is a timing diagram illustrating the adjustment of a relative delay between chirp-packet frequency ramps associated with a chirp-packet drive signal for run-time alignment of a spot scanning wafer inspection system, in accordance with one embodiment of the present disclosure.

FIGS. 6A and 6B illustrate run-time alignment to correct an error in the x-direction (e.g. the direction of motion of the sample stage 120) of a sampling grid associated with a measured object, in accordance with one or more embodiments of the present disclosure. Referring to FIG. 6A, a reference image 602 with a reference sampling grid 604 includes multiple object pixels 606 associated with a reference feature. A measured image 612 without run-time alignment includes multiple object pixels 616 associated with a measured feature. The measured sampling grid 614 without run-time alignment defining the locations of sampled points is misaligned with respect to the reference sampling grid 604. Specifically, object pixels 616 are shifted by approximately ¼ pixels along the x direction with respect to reference image 602. Such a misalignment of the measured sampling grid 614 may, by way of non-limiting example, be caused by inaccurate motion of the sample stage 120 during the measurement process. Run-time alignment adjusts the positions of sampled locations on the measured object to obtain a corrected image 622 with a corrected sampling grid 624 aligned with the reference sampling grid 604. In the corrected image 622, object pixels 626 associated with the measured object are properly aligned.

FIG. 6B illustrates a timing diagram associated with run-time alignment to produce the corrected image 622, in accordance with one or more embodiments of the present disclosure. The misalignment of object pixels 616 is corrected by adjusting the delay 310 between successive scans. Specifically, columns 1-4 of the corrected image 622 are obtained with a nominal delay 310a of 20 time cycles 316 between chirp-packet frequency ramps. Column 5 of the corrected image 622 is obtained with a modified delay 310b of 25 time cycles 316 to compensate for the ¼ pixel shift. Columns 6-11 of the corrected image 622 are obtained with the nominal delay 310a of 20 time cycles 316. In another embodiment, alignment errors in the x direction are adjusted by adjusting the sample stage 120. It is noted herein the alignment errors along the x direction may be adjusted simultaneously with alignment errors along the y direction.

It is noted herein that the above discussions are directed to a spot scanning system in which a single focused illumination spot was scanned across the sample at a given time. These discussions were provided merely for illustrative purposes and should not be interpreted as limiting. In one embodiment, two or more chirp packets sequentially propagate through the acousto-optic deflector such that multiple positions along a scan line 216 are simultaneously illuminated. Such a configuration may be described as a multi-spot scanning system. In another embodiment, a 2-D array of scanning beams 108 simultaneously in focus on the surface of a wafer 112 may be scanned. In another embodiment, a diffractive optical element positioned between a beam deflector 106 and an objective 110 simultaneously splits a scanning beam 108 into multiple scanning beams 108 simultaneously in focus on the wafer 112.

FIG. 7 illustrates a timing diagram illustrating a system 100 with three image acquisition spots associated with three scanning beams 108 simultaneously scanned across a wafer 112, in accordance with one or more embodiments of the present disclosure. The three scanning beams 108 may be generated by any method known in the art. In one embodiment, the three scanning beams 108 are generated by an optical element configured to split a scanning beam 108 into three scanning beams 108 in which the optical element is placed after a beam deflector 106 and prior to an optical objective lens 110. A Image acquisition drive signals 306-1 and sampling drive signal 308-1 are associated with a first scanning beam 108, image acquisition drive signals 306-2 and sampling drive signal 308-2 are associated with a second scanning beam 108, and image acquisition drive signals 306-3 and sampling drive signal 308-3 are associated with a third scanning beam 108. A single chirp-packet drive signal 302 and beam-scanning drive signal 304 are associated with all three spots.

Figure 8A:
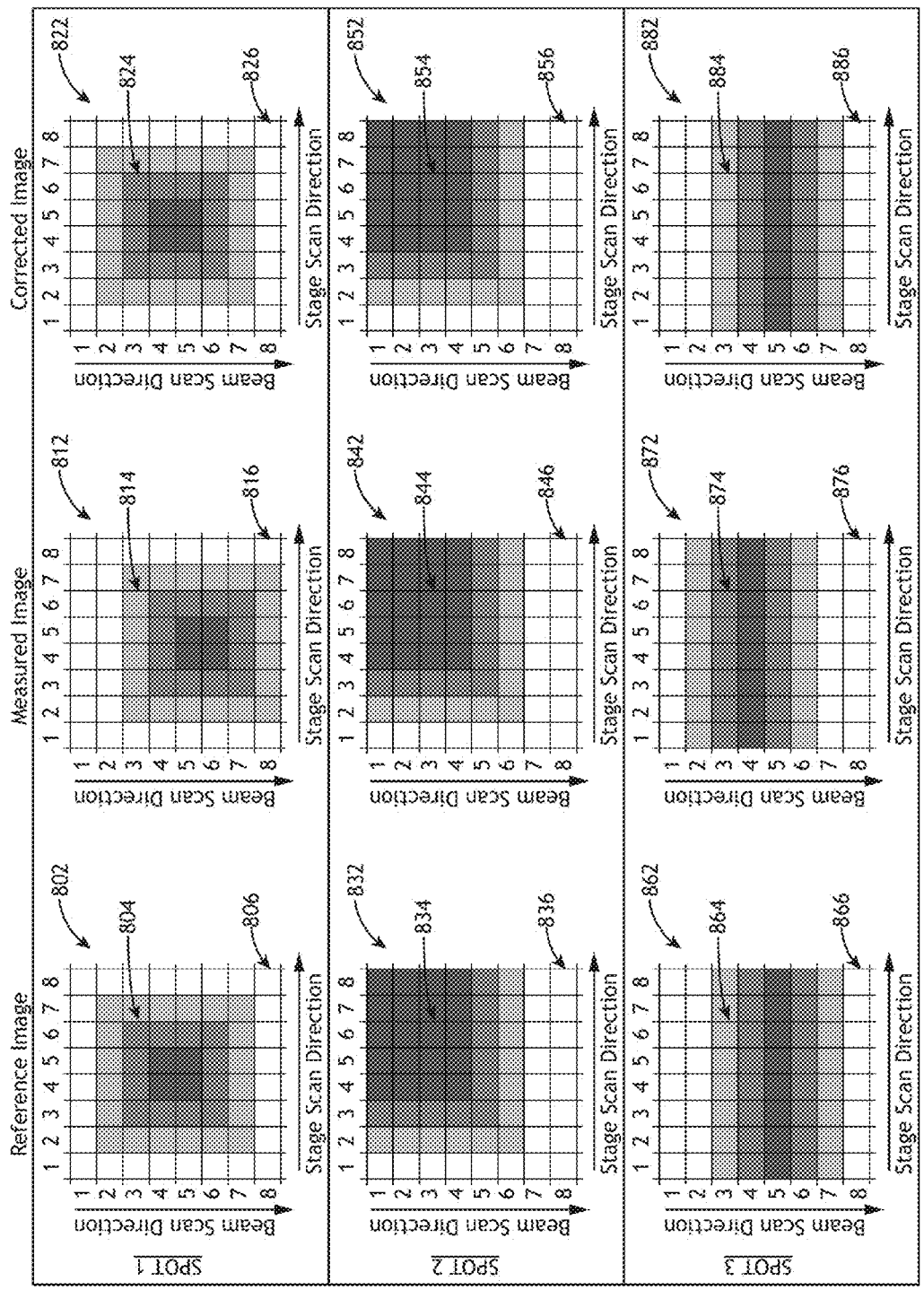
FIG. 8A is a conceptual diagram illustrating run-time alignment of pin-cushion distortion aberration in a multi-spot spot scanning wafer inspection system, in accordance with one embodiment of the present disclosure.
Figure 8B:
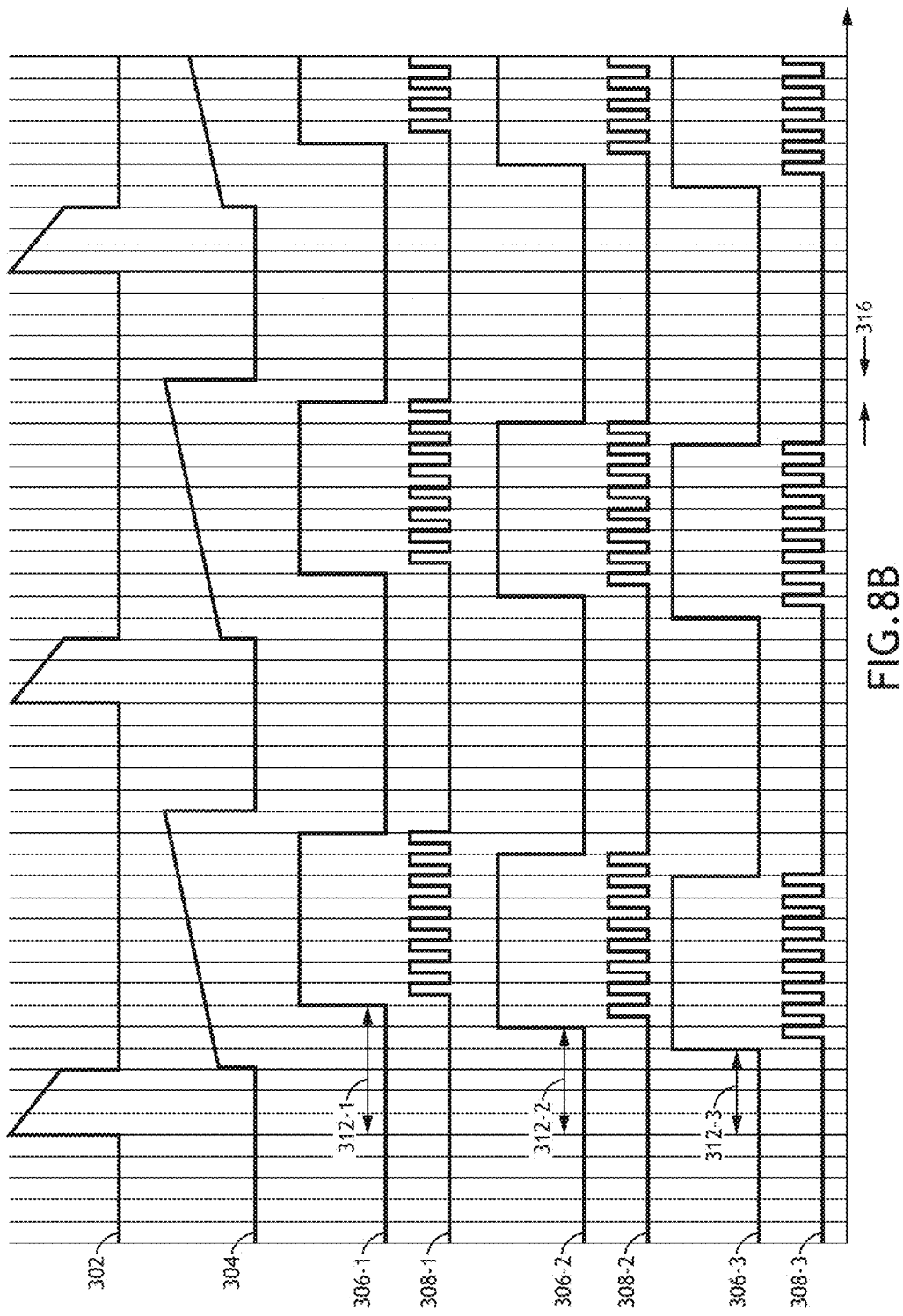
FIG. 8B is a timing diagram illustrating the adjustment of a relative delay between a chirp-packet drive signal and an image acquisition signal for run-time alignment of a multi-spot spot scanning wafer inspection system, in accordance with one embodiment of the present disclosure.

Run-time alignment may be separately applied to each scanning beam 108 in a multi-spot system 100. Further, run time alignment on multiple scanning beams 108 may be used to partially correct imaging aberrations associated with a combined field of view of the multiple scanning beams 108. For example, a multi-spot system 100 may partially correct aberrations including, but not limited to, pin-cushion distortion or barrel distortion. FIGS. 8A and 8B illustrate the partial correction of pin-cushion distortion in a multi-spot system 100, in accordance with one or more embodiments of the present disclosure. FIG. 8A illustrates reference images 802, 832, and 862; measured images 812, 842, and 872 without run-time alignment; and corrected images 822, 852, and 882 associated with a three-spot system 100 with run-time alignment, in accordance with one or more embodiments of the present disclosure. In one embodiment, a first spot is used to generate an image including object pixels 814 associated with a square feature, a second spot is used to generate an image including object pixels 844 associated with a corner feature, and a third spot is used to generate an image including object pixels 874 associated with a line feature. Due to the presence of pin-cushion aberration, object pixels 814 in the measured sampling grid 816 without run-time alignment associated with the first spot are shifted in the −y direction, object pixels 842 in the measured sampling grid 846 without run-time alignment associated with the second spot are accurately imaged, and object pixels 874 in the measured sampling grid 876 without run-time alignment are shifted in the +y direction. Run time alignment adjusts the sample grids 826, 856, and 886 associated with spots 1 and 3 to obtain corrected images 822 and 882 in which the corrected sampling grids 826, 856, and 886 align with reference sampling grids 806, 836, and 866. No aberration-correcting adjustments are made to adjust the corrected sampling grid 856 with respect to the reference sampling grid 836.

FIG. 8B illustrates a timing diagram associated with run-time alignment to produce the corrected images 822, 852, and 882, in accordance with one or more embodiments of the present disclosure. The misalignment of pixels between the three spots is corrected by modifying the image acquisition drive signal delay associated with each spot. Specifically, the corrected image 852 associated with spot 2 is obtained using a nominal delay 312-2, the corrected image 822 associated with spot 1 is obtained using a delay 312-1 one time cycle 316 longer than delay 312-2, and the corrected image 882 associated with spot 3 is obtained using a delay 312-3 one time cycle 316 shorter than delay 312-2.

It is noted herein that a three-spot system 100 associated with FIGS. 7, 8A, and 8B, along with corresponding descriptions above, are provided solely for illustrative purposes and should not be interpreted as limiting. A multi-spot system may include a plurality of scanning beams 108 and associated spots. Further, aberration corrections associated with multiple spots may be adjusted simultaneously with separate adjustments to each spot.

It is noted herein that the set of optics of system 100 as described above and illustrated in FIGS. 1 through 9 are provided merely for illustration and should not be interpreted as limiting. It is anticipated that a number of equivalent or additional optical configurations may be utilized within the scope of the present disclosure. It is further anticipated that one or more optical elements including, but not limited to, circularly symmetric lenses, cylindrical lenses, beam shapers, mirrors, waveplates, polarizers, or filters may be placed in the system. By way of non-limiting example, a cylindrical lens may be placed prior to the beam deflector 106, or alternatively, after the beam deflector 106 in order to modify the spatial profile of the scanning beam 108 on the wafer 112.

Figure 9:
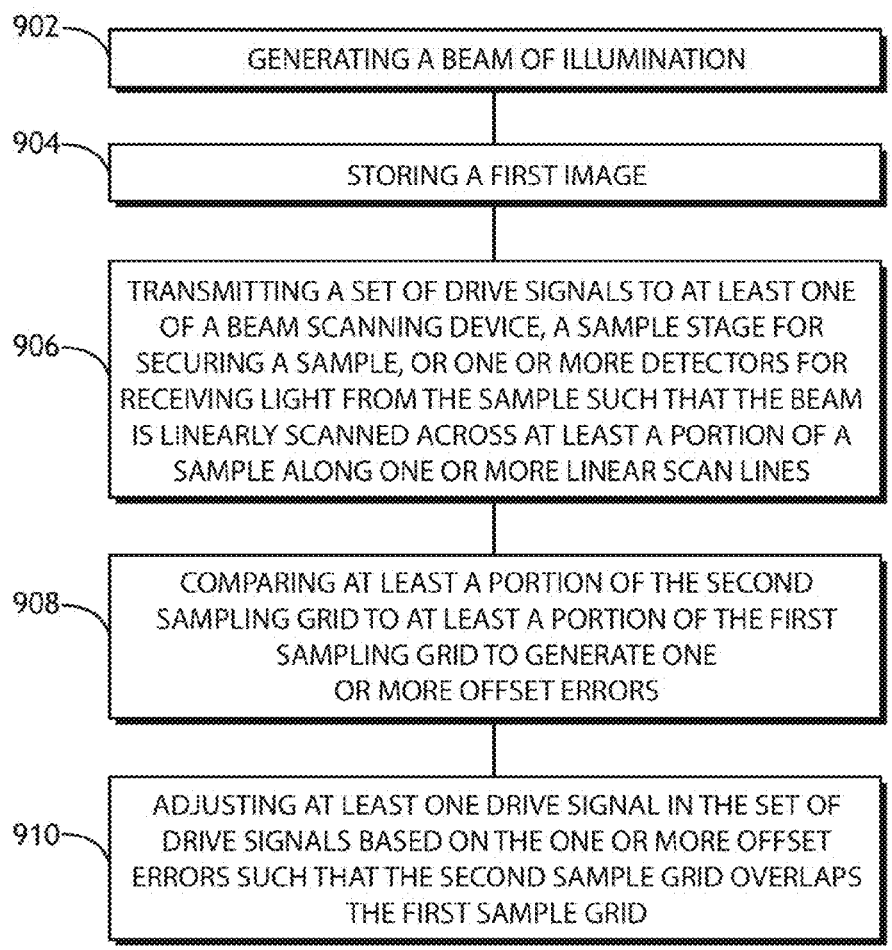
FIG. 9 is a flow diagram illustrating a method for run time alignment of a spot scanning wafer inspection system, in accordance with one embodiment of the present disclosure.

FIG. 9 describes a flow diagram of a method 900 for run-time alignment of a spot scanning wafer inspection system, in accordance with one or more embodiments of the present disclosure. In step 902, a beam of illumination 102 is generated. In step 904, a first image is stored. In one embodiment, the center positions of pixels on the first image define a first sampling grid. In step 906, a set of drive signals (e.g. drive signals 302, 304, 306, and/or 308) is transmitted to at least one of a beam scanning device, a sample stage for securing a sample, or one or more detectors for receiving light from the sample such that the beam is linearly scanned across at least a portion of a sample along one or more linear scan lines. In one embodiment, the sample (e.g. a wafer) is sampled at one or more sampled locations along the one or more linear scan lines based on the set of drive signals to generate a second image. In another embodiment, the one or more sampled locations define a second sampling grid. In another embodiment, data associated with the one or more sampled locations corresponds to one or more pixels of the second image. In step 908, at least a portion of the second sampling grid is compared to at least a portion of the first sampling grid to determine one or more offset errors. In step 910, at least one drive signal in the set of drive signals is adjusted based on the one or more offset errors such that the second sample grid overlaps the first sample grid.

The herein described subject matter sometimes illustrates different components contained within, or connected with, other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically interactable and/or physically interacting components and/or wirelessly interactable and/or wirelessly interacting components and/or logically interactable and/or logically interacting components.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

What is claimed:

1. A spot scanning imaging system with run-time alignment, comprising:
    a beam scanning device configured to linearly scan a beam of illumination across a sample positioned on a sample stage;
    one or more detectors positioned to receive light from the sample; and
    a controller communicatively coupled to the beam scanning apparatus, the sample stage, and the one or more detectors, wherein the controller includes one or more processors configured to execute program instructions to cause the one or more processors to:
        receive a first image, wherein center positions of pixels on the first image define a first sampling grid;
        transmit beam-scanning drive signals to at least one of the beam scanning device or the sample stage to scan the beam across at least a portion of the sample along one or more scan lines;
        transmit image acquisition drive signals to the one or more detectors to generate image data associated with light received from one or more selected locations on the sample corresponding to the first sampling grid, wherein the one or more detectors generate image data associated with light received from one or more sampled locations, wherein the one or more sampled locations define a second sampling grid and correspond to one or more pixels of a second image;
        compare at least a portion of the second sampling grid to at least a portion of the first sampling grid on the fly to determine one or more sampling offset errors; and
        adjust, with at least one of the beam-scanning drive signals or the image acquisition drive signals, the second sample grid on the fly to overlap the first sample grid based on the one or more sampling offset errors.

2. The system of claim 1, wherein adjusting the second sample grid on the fly to overlap the first sample grid based on the one or more sampling offset errors comprises:
    adjusting a relative delay of the image acquisition drive signals with respect to the beam-scanning drive signals.

3. The system of claim 2, wherein adjusting the relative delay of the image acquisition drive signals with respect to the beam-scanning drive signals individually adjusts the one or more sampled locations along the one or more scan lines.

4. The system of claim 1, wherein the beam scanning device includes an acousto-optic deflector, wherein the acousto-optic deflector is configured to generate a chirp packet that propagates along a length of the acousto-optic deflector, wherein the chirp packet focuses and scans at least a portion of the beam along an intermediate scan line, wherein the system further comprises:
    a relay lens assembly including one or more lenses positioned to relay the focused and scanned beam from the intermediate scan line to the sample as a scan line of the one or more scan lines.

5. The system of claim 4, wherein adjusting the second sample grid on the fly to overlap the first sample grid based on the one or more sampling offset errors comprises:
    adjusting at least one of a start position or an end position of a scan line of the one or more scan lines by adjusting at least one of a start frequency or an end frequency of the chirp packet.

6. The system of claim 5, wherein the start frequency and the end frequency are simultaneously adjusted such that a bandwidth of the chirp packet remains constant.

7. The system of claim 6, wherein the at least a portion of the beam focused by the chirp packet maintains a constant axial focal position on the sample.

8. The system of claim 1, wherein a spot size of the beam on the sample is independent of a position of the beam on the sample.

9. The system of claim 1, wherein a defect detection sensitivity is independent of a position of the beam on the sample.

10. The system of claim 1, wherein the beam scanning device includes at least one of an acousto-optic beam deflector, an electro-optic beam deflector, a polygonal scanner, a resonant scanner, or a galvanometer scanner.

11. The system of claim 1, wherein the beam scanning device includes an objective lens positioned to focus the beam onto the sample.

12. A spot scanning imaging system with run-time alignment, comprising:
    an illumination source configured to generate a beam of illumination;
    an acousto-optic deflector, wherein the acousto-optic deflector is configured to generate a chirp packet that propagates along a length of the acousto-optic deflector, wherein the chirp packet focuses and scans at least a portion of the beam along an intermediate scan line;
    a relay lens assembly including one or more lenses positioned to relay the focused and scanned beam to a sample secured on a sample stage;
    one or more detectors positioned to receive light from the sample; and
    a controller communicatively coupled to the acousto-optic deflector and at least one of the one or more detectors, wherein the controller includes one or more processors configured to execute program instructions configured to cause the one or more processors to:
        receive a first image, wherein center positions of pixels on the first image define a first sampling grid;
        transmit beam-scanning drive signals to at least one of the beam scanning device or the sample stage to scan the beam across at least a portion of the sample along one or more linear scan lines;
        transmit image acquisition drive signals to the one or more detectors to generate image data associated with light received from one or more selected locations on the sample corresponding to the first sampling grid, wherein the one or more detectors generate image data associated with light received from one or more sampled locations, wherein the one or more sampled locations define a second sampling grid and correspond to one or more pixels of a second image;

compare at least a portion of the second sampling grid to at least a portion of the first sampling grid on the fly to determine one or more sampling offset errors; and adjust, with at least one of the beam-scanning drive signals or the image acquisition drive signals in the set of drive signals, the second sample grid on the fly to overlap the first sample grid based on the one or more sampling offset sampling errors.

13. The system of claim 12, wherein adjusting at least one of a start position or an end position of a scan line of the one or more scan lines by adjusting at least one of a start frequency or an end frequency of the chirp packet.

14. The system of claim 13, wherein the start frequency and the end frequency are simultaneously adjusted such that a bandwidth of the chirp packet remains constant.

15. The system of claim 14, wherein the at least a portion of the beam focused by the chirp packet maintains a constant axial focal position on the sample.

16. The system of claim 12, wherein a duration of a drive signal associated with the acousto-optic beam deflector is less than a time required for the chirp packet to propagate across the acousto-optic deflector.

17. The system of claim 12, wherein the acousto-optic deflector simultaneously generates two or more chirp packets that propagate across the acousto-optic deflector in sequence, wherein the two or more chirp packets simultaneously focus and scan two or more portions of the beam along the intermediate scan line.

18. The system of claim 12, wherein adjusting the second sample grid on the fly to overlap the first sample grid based on the one or more sampling offset errors comprises:

adjusting a relative delay of the image acquisition drive signals with respect to the beam-scanning drive signals.

19. The system of claim 18, wherein adjusting the relative delay of the image acquisition drive signals with respect to the beam-scanning drive signals individually adjusts the one or more sampled locations along the one or more scan lines.

20. The system of claim 12, wherein the relay lens assembly includes a relay lens positioned to collimate the beam focused and scanned along the intermediate linear path, wherein the relay lens assembly further includes an objective lens positioned to focus the beam onto the sample.

21. The system of claim 20, wherein an optical axis of the objective lens is shifted from an optical axis of the relay lens, and wherein a focal plane of the objective lens is parallel and proximate to the sample.

22. The system of claim 12, further comprising:

a beam scanner positioned prior to the acousto-optic beam deflector such that the beam scanner directs the beam to the chirp packet propagating across the length of the acousto-optic beam deflector to continuously illuminate the chirp packet.

23. The system of claim 12, wherein the beam scanner comprises:

at least one of an acousto-optic beam deflector, an electro-optic beam deflector, a polygonal scanner, a resonant scanner, or a galvanometer scanner.

24. A method for run-time alignment of a spot scanning sample inspection system, comprising:

generating a beam of illumination;

receiving a first image, wherein center positions of pixels on the first image define a first sampling grid;

transmitting beam-scanning drive signals to at least one of a beam scanning device or a sample stage for securing a sample to scan the beam across at least a portion of the sample along one or more scan lines;

transmitting image acquisition drive signals to the one or more detectors to generate image data associated with light received from one or more selected locations on the sample corresponding to the first sampling grid, wherein the one or more detectors generate image data associated with light received from one or more sampled locations, wherein the one or more sampled locations define a second sampling grid and correspond to one or more pixels of the second image;

comparing at least a portion of the second sampling grid to at least a portion of the first sampling grid on the fly to determine one or more sampling offset errors; and adjusting with at least one of the beam-scanning drive signals or the image acquisition drive signals, the second sample grid on the fly to overlap the first sample grid based on the one or more sampling offset errors.

25. The system of claim 24, wherein adjusting the second sample grid on the fly to overlap the first sample grid based on the one or more sampling offset errors comprises:

adjusting a relative delay of the image acquisition drive signals with respect to the beam-scanning drive signals.

26. The method of claim 24, wherein the beam scanning device comprises:

an acousto-optic deflector, wherein the acousto-optic deflector is configured to generate a chirp packet that propagates along a length of the acousto-optic deflector, wherein the chirp packet focuses and scans at least a portion of the beam, wherein adjusting the second sample grid on the fly to overlap the first sample grid based on the one or more sampling offset errors comprises:

adjusting at least one of a start frequency or an end frequency of the chirp packet.

* * * * *